United States Patent
Twomey

(10) Patent No.: US 9,649,121 B2
(45) Date of Patent: *May 16, 2017

(54) APPARATUS FOR PERFORMING AN ELECTROSURGICAL PROCEDURE

(71) Applicant: COVIDIEN LP, Mansfield, MA (US)

(72) Inventor: John R. Twomey, Superior, CO (US)

(73) Assignee: COVIDIEN LP, Mansfield, MA (US)

( * ) Notice: Subject to any disclaimer, the term of this patent is extended or adjusted under 35 U.S.C. 154(b) by 277 days.

This patent is subject to a terminal disclaimer.

(21) Appl. No.: 14/507,365

(22) Filed: Oct. 6, 2014

(65) Prior Publication Data
US 2015/0025570 A1    Jan. 22, 2015

Related U.S. Application Data

(63) Continuation of application No. 13/111,642, filed on May 19, 2011, now Pat. No. 8,852,185.

(51) Int. Cl.
*A61B 18/12* (2006.01)
*A61B 17/29* (2006.01)
(Continued)

(52) U.S. Cl.
CPC .......... *A61B 17/29* (2013.01); *A61B 18/1445* (2013.01); *A61B 2017/2929* (2013.01);
(Continued)

(58) Field of Classification Search
CPC . A61B 17/29; A61B 17/2909; A61B 18/1445; A61B 18/1442; A61B 18/1447;
(Continued)

(56) References Cited

U.S. PATENT DOCUMENTS

D249,549 S   9/1978 Pike
D263,020 S   2/1982 Rau, III
(Continued)

FOREIGN PATENT DOCUMENTS

CN   201299462   9/2009
DE   2415263 A1   10/1975
(Continued)

OTHER PUBLICATIONS

U.S. Appl. No. 08/926,869, filed Sep. 10, 1997, James G. Chandler.
(Continued)

*Primary Examiner* — Daniel Fowler

(57) ABSTRACT

An endoscopic forceps includes a housing having a shaft extending therefrom for treating tissue. A longitudinal axis is defined through the shaft. An end effector assembly is operably coupled to a distal end of the shaft and includes a pair of first and second jaw members. A rotating assembly operably coupled to the shaft is configured to rotate the shaft and the end effector about the longitudinal axis. A drive assembly is configured to selectively and releasably engage the rotating assembly. Engagement of the rotating assembly with the drive assembly couples the rotating assembly to the shaft such that the shaft is rotatable about the longitudinal axis in a predetermined direction when the rotating assembly is rotated. And, disengagement of the rotating assembly from the drive assembly uncouples the rotating assembly from the shaft such that the shaft is non-rotatable about the longitudinal axis when the rotating assembly is rotated.

29 Claims, 4 Drawing Sheets

(51) Int. Cl.
*A61B 18/14* (2006.01)
*A61B 18/00* (2006.01)

(52) U.S. Cl.
CPC .............. *A61B 2017/2947* (2013.01); *A61B 2018/00202* (2013.01)

(58) Field of Classification Search
CPC .............. A61B 2017/291–2017/2948; A61B 2018/00202; A61B 2018/145; A61B 2018/1452; A61B 2018/1455; A61B 2018/1457; A61B 2018/146
See application file for complete search history.

(56) References Cited

U.S. PATENT DOCUMENTS

| | | |
|---|---|---|
| 4,331,277 A | 5/1982 | Green |
| 4,606,343 A | 8/1986 | Conta et al. |
| 4,644,950 A | 2/1987 | Valli |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 4,936,845 A | 6/1990 | Stevens |
| 5,237,884 A | 8/1993 | Seto |
| 5,249,583 A | 10/1993 | Mallaby |
| D343,453 S | 1/1994 | Noda |
| 5,282,806 A | 2/1994 | Haber et al. |
| 5,312,023 A | 5/1994 | Green et al. |
| D348,930 S | 7/1994 | Olson |
| 5,326,013 A | 7/1994 | Green et al. |
| D349,341 S | 8/1994 | Lichtman et al. |
| 5,350,355 A | 9/1994 | Sklar |
| 5,352,235 A | 10/1994 | Koros et al. |
| D354,564 S | 1/1995 | Medema |
| 5,381,943 A | 1/1995 | Allen et al. |
| 5,389,098 A | 2/1995 | Tsuruta et al. |
| D358,887 S | 5/1995 | Feinberg |
| 5,467,911 A | 11/1995 | Tsuruta et al. |
| 5,518,163 A | 5/1996 | Hooven |
| 5,518,164 A | 5/1996 | Hooven |
| 5,591,170 A | 1/1997 | Spievack et al. |
| 5,628,446 A | 5/1997 | Geiste et al. |
| 5,653,374 A | 8/1997 | Young et al. |
| D384,413 S | 9/1997 | Zlock et al. |
| 5,667,517 A | 9/1997 | Hooven |
| 5,779,130 A | 7/1998 | Alesi et al. |
| 5,782,397 A | 7/1998 | Koukline |
| H1745 H | 8/1998 | Paraschac |
| D402,028 S | 12/1998 | Grimm et al. |
| D408,018 S | 4/1999 | McNaughton |
| 5,893,835 A * | 4/1999 | Witt .............. A61B 17/320092 601/2 |
| 5,954,259 A | 9/1999 | Viola et al. |
| 5,954,731 A | 9/1999 | Yoon |
| D416,089 S | 11/1999 | Barton et al. |
| D424,694 S | 5/2000 | Tetzlaff et al. |
| D425,201 S | 5/2000 | Tetzlaff et al. |
| 6,119,913 A | 9/2000 | Adams et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| 6,461,372 B1 | 10/2002 | Jensen et al. |
| D465,281 S | 11/2002 | Lang |
| D466,209 S | 11/2002 | Bon |
| 6,533,157 B1 | 3/2003 | Whitman |
| 6,699,177 B1 | 3/2004 | Wang et al. |
| 6,716,233 B1 | 4/2004 | Whitman |
| D493,888 S | 8/2004 | Reschke |
| D496,997 S | 10/2004 | Dycus et al. |
| D499,181 S | 11/2004 | Dycus et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| D502,994 S | 3/2005 | Blake, III |
| D509,297 S | 9/2005 | Wells |
| 6,953,139 B2 | 10/2005 | Milliman et al. |
| 6,981,941 B2 | 1/2006 | Whitman et al. |
| D525,361 S | 7/2006 | Hushka |
| 7,111,769 B2 | 9/2006 | Wales et al. |
| D531,311 S | 10/2006 | Guerra et al. |
| 7,128,253 B2 | 10/2006 | Mastri et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| 7,422,136 B1 | 9/2008 | Marczyk |
| D582,038 S | 12/2008 | Swoyer et al. |
| 7,461,767 B2 | 12/2008 | Viola et al. |
| 7,464,846 B2 | 12/2008 | Shelton, IV et al. |
| 7,556,185 B2 | 7/2009 | Viola |
| 7,648,055 B2 | 1/2010 | Marczyk |
| 7,708,182 B2 | 5/2010 | Viola |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,753,248 B2 | 7/2010 | Viola |
| 7,757,925 B2 | 7/2010 | Viola et al. |
| D621,503 S | 8/2010 | Otten et al. |
| 7,789,283 B2 | 9/2010 | Shah |
| D627,462 S | 11/2010 | Kingsley |
| D628,289 S | 11/2010 | Romero |
| D628,290 S | 11/2010 | Romero |
| D630,324 S | 1/2011 | Reschke |
| 7,909,221 B2 | 3/2011 | Viola et al. |
| 7,950,560 B2 | 5/2011 | Zemlok et al. |
| 8,128,625 B2 | 3/2012 | Odom |
| 8,147,489 B2 | 4/2012 | Moses et al. |
| 8,298,233 B2 | 10/2012 | Mueller |
| 8,394,096 B2 | 3/2013 | Moses et al. |
| 8,409,246 B2 | 4/2013 | Kerr et al. |
| 8,409,247 B2 | 4/2013 | Garrison et al. |
| 8,425,511 B2 | 4/2013 | Olson |
| 8,430,877 B2 | 4/2013 | Kerr et al. |
| 8,439,913 B2 | 5/2013 | Horner et al. |
| 8,469,716 B2 | 6/2013 | Fedotov et al. |
| 8,469,991 B2 | 6/2013 | Kerr |
| 8,469,992 B2 | 6/2013 | Roy et al. |
| 8,491,624 B2 | 7/2013 | Kerr et al. |
| 8,491,625 B2 | 7/2013 | Horner |
| 8,491,626 B2 | 7/2013 | Roy et al. |
| 8,512,336 B2 | 8/2013 | Couture |
| 8,540,749 B2 | 9/2013 | Garrison et al. |
| 8,551,091 B2 | 10/2013 | Couture et al. |
| 8,556,929 B2 | 10/2013 | Harper et al. |
| 8,568,397 B2 | 10/2013 | Horner et al. |
| 8,568,408 B2 | 10/2013 | Townsend et al. |
| 8,585,736 B2 | 11/2013 | Horner et al. |
| 8,597,295 B2 | 12/2013 | Kerr |
| 8,623,018 B2 | 1/2014 | Horner et al. |
| 8,628,557 B2 | 1/2014 | Collings et al. |
| 8,641,712 B2 | 2/2014 | Couture |
| 8,647,343 B2 | 2/2014 | Chojin et al. |
| 8,652,135 B2 | 2/2014 | Nau, Jr. |
| 8,663,222 B2 | 3/2014 | Anderson et al. |
| 8,672,939 B2 | 3/2014 | Garrison |
| 8,685,009 B2 | 4/2014 | Chernov et al. |
| 8,685,021 B2 | 4/2014 | Chernov et al. |

(56) References Cited

U.S. PATENT DOCUMENTS

| | | |
|---|---|---|
| 8,702,749 B2 | 4/2014 | Twomey |
| 8,734,445 B2 | 5/2014 | Johnson et al. |
| 8,740,898 B2 | 6/2014 | Chojin et al. |
| 8,745,840 B2 | 6/2014 | Hempstead et al. |
| 8,784,418 B2 | 7/2014 | Romero |
| 8,795,269 B2 | 8/2014 | Garrison |
| 8,808,288 B2 | 8/2014 | Reschke |
| 8,814,864 B2 | 8/2014 | Gilbert |
| 8,840,639 B2 | 9/2014 | Gerhardt, Jr. et al. |
| 8,852,185 B2 | 10/2014 | Twomey |
| 8,858,553 B2 | 10/2014 | Chojin |
| 8,888,771 B2 | 11/2014 | Twomey |
| 8,888,775 B2 | 11/2014 | Nau, Jr. et al. |
| 8,900,232 B2 | 12/2014 | Ourada |
| 8,906,018 B2 | 12/2014 | Rooks et al. |
| 2010/0252610 A1 | 10/2010 | Viola |
| 2011/0018164 A1 | 1/2011 | Sartor et al. |
| 2011/0193608 A1 | 8/2011 | Krapohl |
| 2011/0251605 A1 | 10/2011 | Hoarau et al. |
| 2011/0270245 A1 | 11/2011 | Horner et al. |
| 2011/0270251 A1 | 11/2011 | Horner et al. |
| 2011/0276048 A1 | 11/2011 | Kerr et al. |
| 2011/0276049 A1 | 11/2011 | Gerhardt |
| 2011/0295313 A1 | 12/2011 | Kerr |
| 2011/0319888 A1 | 12/2011 | Mueller et al. |
| 2012/0059372 A1 | 3/2012 | Johnson |
| 2012/0059375 A1 | 3/2012 | Couture et al. |
| 2012/0059408 A1 | 3/2012 | Mueller |
| 2012/0059409 A1 | 3/2012 | Reschke et al. |
| 2012/0083785 A1 | 4/2012 | Roy et al. |
| 2012/0083786 A1 | 4/2012 | Artale et al. |
| 2012/0083827 A1 | 4/2012 | Artale et al. |
| 2012/0123402 A1 | 5/2012 | Chernov et al. |
| 2012/0123404 A1 | 5/2012 | Craig |
| 2012/0123410 A1 | 5/2012 | Craig |
| 2012/0130367 A1 | 5/2012 | Garrison |
| 2012/0136354 A1 | 5/2012 | Rupp |
| 2012/0172868 A1 | 7/2012 | Twomey et al. |
| 2012/0172924 A1 | 7/2012 | Allen, IV |
| 2012/0184989 A1 | 7/2012 | Twomey |
| 2012/0215219 A1 | 8/2012 | Roy et al. |
| 2012/0239034 A1 | 9/2012 | Horner et al. |
| 2012/0253344 A1 | 10/2012 | Dumbauld et al. |
| 2012/0259331 A1 | 10/2012 | Garrison |
| 2012/0283727 A1 | 11/2012 | Twomey |
| 2012/0296205 A1 | 11/2012 | Chernov et al. |
| 2012/0296238 A1 | 11/2012 | Chernov et al. |
| 2012/0296239 A1 | 11/2012 | Chernov et al. |
| 2012/0296317 A1 | 11/2012 | Chernov et al. |
| 2012/0296323 A1 | 11/2012 | Chernov et al. |
| 2012/0296324 A1 | 11/2012 | Chernov et al. |
| 2012/0296334 A1 | 11/2012 | Kharin |
| 2012/0303025 A1 | 11/2012 | Garrison |
| 2012/0323238 A1 | 12/2012 | Tyrrell et al. |
| 2012/0330308 A1 | 12/2012 | Joseph |
| 2012/0330309 A1 | 12/2012 | Joseph |
| 2013/0018364 A1 | 1/2013 | Chernov et al. |
| 2013/0018372 A1 | 1/2013 | Sims et al. |
| 2013/0022495 A1 | 1/2013 | Allen, IV et al. |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 10045375 C2 | 10/2002 |
| DE | 202007009165 U1 | 8/2007 |
| DE | 202007009317 U1 | 8/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1 159 926 A2 | 12/2001 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-317934 A | 12/1996 |
| JP | 9-10223 C | 1/1997 |
| JP | 9-122138 A | 5/1997 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000342599 A | 12/2000 |
| JP | 2000350732 A | 12/2000 |
| JP | 2001-8944 | 1/2001 |
| JP | 2001-29356 | 2/2001 |
| JP | 2001128990 A | 5/2001 |
| JP | 2001-190564 A | 7/2001 |
| JP | 2004-517668 A | 6/2004 |
| JP | 2004-528869 A | 9/2004 |
| SU | 401367 A1 | 10/1973 |
| WO | 0036986 A1 | 6/2000 |
| WO | 0115614 A1 | 3/2001 |
| WO | 0154604 A1 | 8/2001 |
| WO | 2005/110264 A2 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967, British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).

(56) References Cited

OTHER PUBLICATIONS

Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 11 152220.7 dated May 19, 2011.
Int'l Search Report EP 11 152360.1 dated Jun. 6, 2011.
Int'l Search Report EP 11 161117.4 dated Jun. 30, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.

(56) References Cited

OTHER PUBLICATIONS

Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 185386.9 dated Jan. 10, 2011.
Int'l Search Report EP 10 185405.7 dated Jan. 5, 2011.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182022.3 dated Mar. 11, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.

\* cited by examiner

APPARATUS FOR PERFORMING AN ELECTROSURGICAL PROCEDURE

This application is a continuation application of U.S. patent application Ser. No. 13/111,642, filed on May 19, 2011, the entire contents of which are hereby incorporated herein by reference.

BACKGROUND

The present disclosure relates to an apparatus for performing an electrosurgical procedure. More particularly, the present disclosure relates to an endoscopic forceps including a shaft and a rotating assembly that is releasably and selectively engageable with a drive assembly of an endoscopic for rotating the shaft when the rotating assembly is rotated.

DESCRIPTION OF RELATED ART

Electrosurgical instruments, e.g., endoscopic forceps, are well known in the medical arts and typically include a housing, a handle assembly including a movable handle, a shaft and an end effector assembly attached to a distal end of the shaft. The end effector includes jaw members configured to manipulate tissue (e.g., grasp and seal tissue). Typically, the endoscopic forceps utilizes both mechanical clamping action and electrical energy to effect hemostasis by heating the tissue and blood vessels to coagulate, cauterize, seal, cut, desiccate, and/or fulgurate tissue. Usually, one or more driving mechanisms, e.g., a drive assembly including a drive element, is utilized to cooperate with one or more components operatively associated with the handle assembly to impart movement to one or both of the jaw members. To facilitate positioning the jaw members about tissue, the endoscopic forceps sometimes includes a rotating assembly. The rotating assembly is usually operably coupled to the shaft and configured such that rotation of the rotating assembly rotates the shaft including the jaw members thereon in a predetermined direction, e.g., approximately 180° in either a clockwise or counterclockwise direction.

Under certain surgical scenarios, it may prove advantageous to have the rotating assembly temporarily disabled. For example, after a surgeon has positioned tissue between the jaw members, the jaw members are typically approximated toward one another and locked into a clamping position via one or more suitable locking methods, e.g., the movable handle is moved into a locked position. In the clamping position, and with the rotating assembly enabled, there exists the possibility of the rotating assembly being inadvertently rotated, which, in turn, may result in the shaft including the jaw members rotating. As can be appreciated, inadvertent or unwanted rotation of the shaft and/or jaw members during an electrosurgical procedure may result in tissue being ineffectively electrosurgically treated, e.g., an ineffective thrombosis may be formed along a tissue seal.

SUMMARY

The present disclosure provides an endoscopic forceps. The endoscopic forceps includes a housing having a shaft extending therefrom for treating tissue. The shaft defines a longitudinal axis therethrough. An end effector assembly operably coupled to a distal end of the shaft includes a pair of first and second jaw members. A rotating assembly operably coupled to the shaft is configured to rotate the shaft including the end effector about the longitudinal axis. A drive assembly is configured to selectively and releasably engage the rotating assembly such that engagement of the rotating assembly with the drive assembly couples the rotating assembly to the shaft such that the shaft is rotatable about the longitudinal axis in a predetermined direction when the rotating assembly is rotated. And, disengagement of the rotating assembly from the drive assembly uncouples the rotating assembly from the shaft such that the shaft is non-rotatable about the longitudinal axis when the rotating assembly is rotated.

The present disclosure provides an endoscopic forceps. The endoscopic forceps includes a housing having a shaft extending therefrom for treating tissue. The shaft defines a longitudinal axis therethrough. An end effector assembly operably coupled to a distal end of the shaft includes a pair of first and second jaw members. A rotating assembly operably coupled to the shaft is configured to rotate the shaft including the end effector about the longitudinal axis. A drive assembly is configured to selectively and releasably engage the rotating assembly such that engagement of the rotating assembly with the drive assembly couples the rotating assembly to the shaft such that the shaft is rotatable about the longitudinal axis in a predetermined direction when the rotating assembly is rotated. And, disengagement of the rotating assembly from the drive assembly uncouples the rotating assembly from the shaft such that the shaft is non-rotatable about the longitudinal axis when the rotating assembly is rotated. A mandrel is coaxially positioned about an outer tube of the shaft and configured to support a proximal external gear wheel of the rotating assembly and the drive assembly thereon.

BRIEF DESCRIPTION OF THE DRAWING

Various embodiments of the present disclosure are described hereinbelow with references to the drawings, wherein.

DETAILED DESCRIPTION

Figure 1:
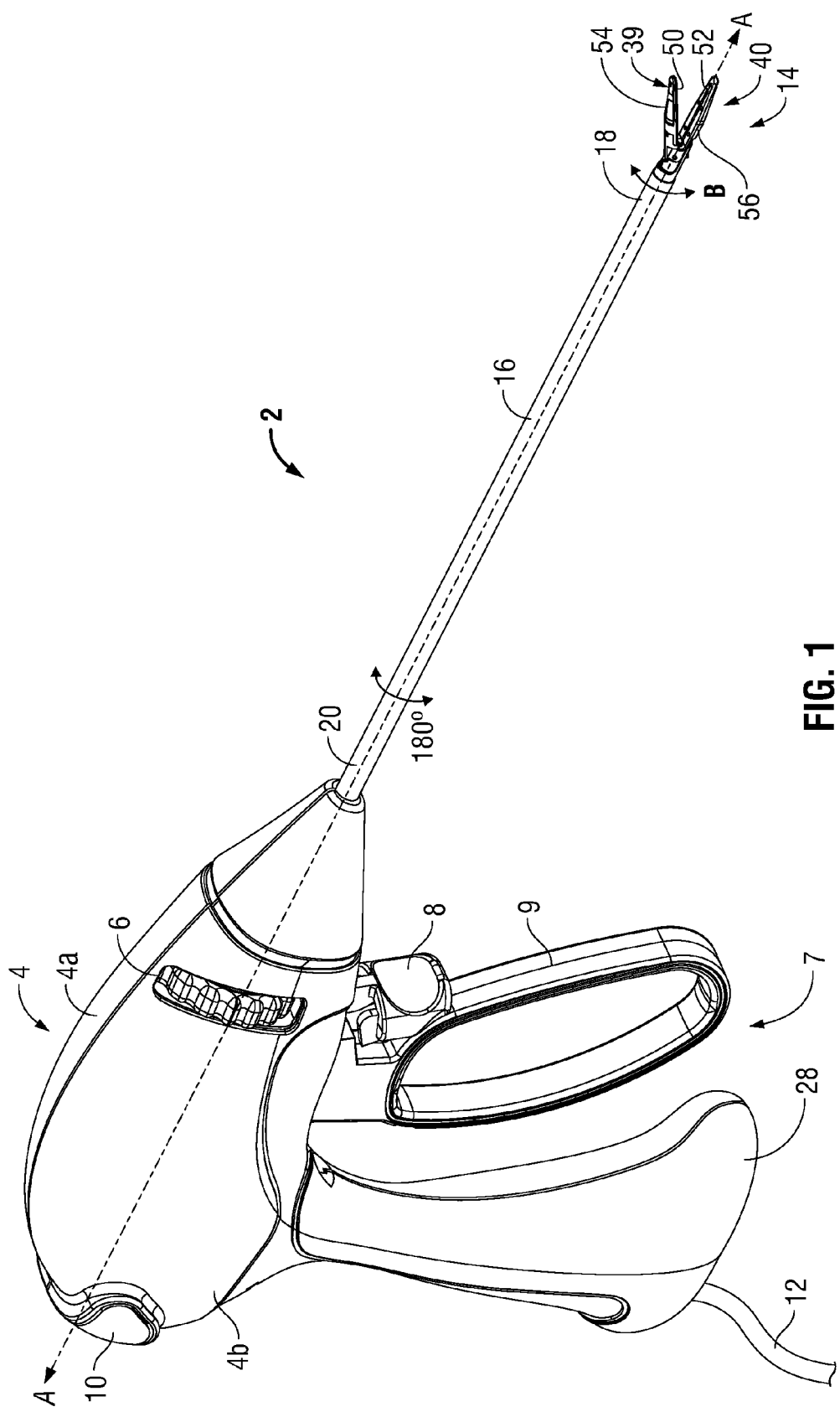
FIG. 1 is a perspective view of an endoscopic forceps including a housing, a shaft, a handle assembly, a rotating assembly and an end effector assembly shown in an open configuration according to an embodiment of the present disclosure.

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, will refer to an end of a surgical instrument that is closer to the user, while the term "distal" will refer to an end of the surgical instrument that is farther from the user.

FIG. 1 shows in detail the operating features and inter-cooperating components of an endoscopic bipolar forceps generally identified as forceps 2. Briefly, forceps 2 is for use with various surgical procedures and includes: a housing 4, a rotating assembly 6, a trigger assembly 8, a switch 10, an electrosurgical cable 12 for connecting the forceps 2 to an electrosurgical generator (not shown), a drive assembly 30 (FIG. 2), a handle assembly 7, and an end effector assembly 14. These various components mutually cooperate to grasp, seal and divide tubular vessels and vascular tissues. For a more detailed description of the trigger assembly 8, switch 10, and electrosurgical cable 12, reference is made to commonly-owned U.S. Pat. No. 7,156,846 to Dycus et al. filed on Jun. 13, 2003.

With continued reference to FIG. 1, housing 4 includes housing halves 4a and 4b that include a plurality of interfaces (not explicitly shown) that are dimensioned to mechanically align and engage one another to form housing 4 and enclose the internal working components of forceps 2.

Figure 2:
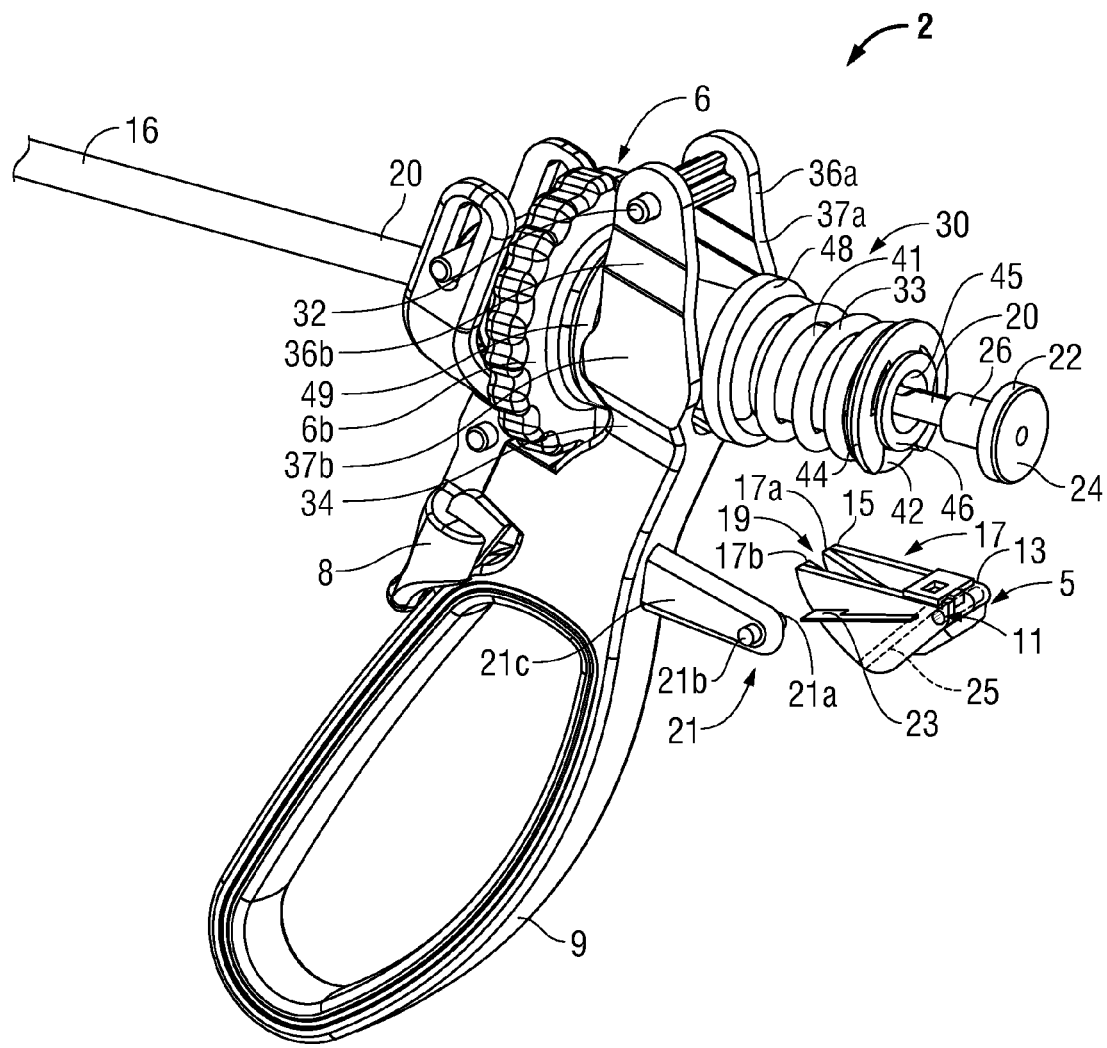
FIG. 2 is a partial, left perspective view of the endoscopic forceps of FIG. 1 shown with the housing removed to illustrate the rotating assembly in an engaged position.
Figure 3:
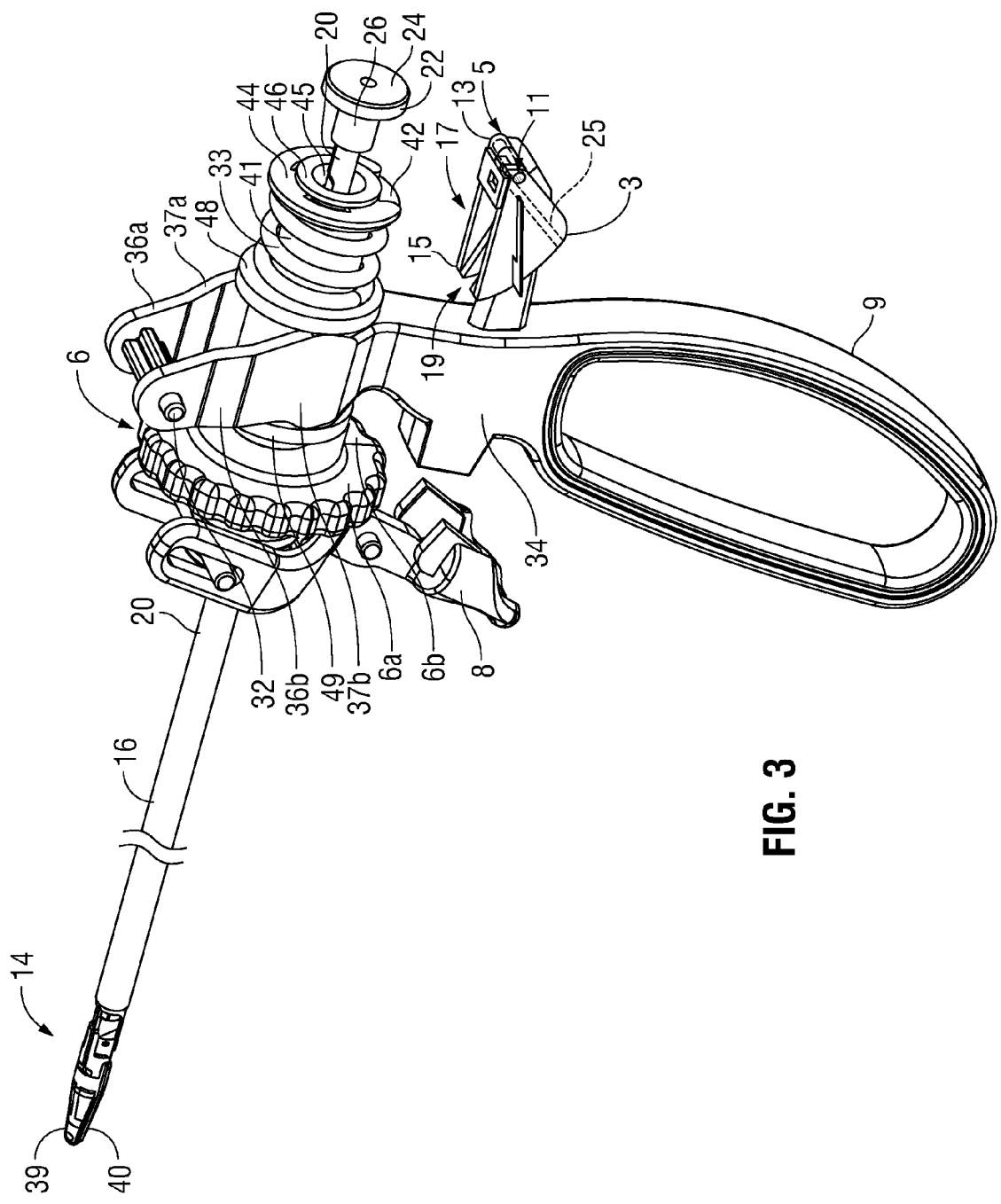
FIG. 3 is a left perspective view illustrating the rotating assembly in a disengaged position.

With reference to FIGS. 2 and 3, a latch 5 is configured to releasably engage a movable handle 9 of the handle assembly 7. With this purpose in mind, latch 5 operably and pivotably couples, via one or more suitable coupling methods, to an internal frame of the housing 4. In the illustrated embodiment, a pivot pin (not explicitly shown) operably couples to a corresponding aperture 11 that extends transversely through a proximal end 13 of the latch 5 for fixedly coupling the latch 5 to the internal frame of the housing 4.

One or more resilient members, e.g., a leaf spring 23, are operably coupled to the latch 5 and configured to bias the latch 5 in an upwardly direction (FIGS. 2 and 3). More particularly, a leaf spring 23 extends substantially along a length of an outer surface of the latch 5 (FIGS. 2 and 3) and provides an upward biasing force that urges the latch 5 upward.

A distal end 15 of the latch 5 includes a generally slanted bifurcated ramp portion 17 that is defined by individual ramp portions 17a and 17b (FIG. 2) that collectively define an opening 19 therebetween (FIGS. 2 and 3). The ramp portions 17a and 17b are configured to slidably engage corresponding locking pins 21a and 21b of a locking feature 21 operably coupled to the movable handle 9 (FIG. 2). Opening 19 is configured to receive an elongated portion 21c (FIG. 2) of the locking feature 21 therein (FIG. 3). Proximal ends of each of the ramp portions 17a and 17b are configured to releasably engage the corresponding locking pins 21a and 21b. More particularly, a generally elongated cavity 25 (shown phantomly in FIGS. 2 and 3) extends transversely along an interior of the latch 5 adjacent the proximal ends of the ramp portions 17a and 17b. To facilitate engaging and disengaging the locking pins 21a and 21b from the cavity 25, the cavity 25 includes a contour that corresponds to a contour of the locking pins 21a and 21b, i.e., cavity 25 includes a generally arcuate or concave configuration. The generally arcuate configuration of the contour 25 is exhibited on an exterior surface 3 (FIG. 3) at the proximal end of the latch 5 and is configured to contact the internal frame of the housing 4 to facilitate pivoting of the latch 5 about the internal frame of the housing 4.

Referring again to FIG. 1, forceps 2 includes a shaft 16 that defines a longitudinal axis "A-A" therethrough. Shaft 16 includes a distal end 18 configured to mechanically engage the end effector assembly 14 (FIG. 1) operably associated with the forceps 2 and a proximal end 20 that mechanically engages the housing 4 (FIG. 1). More particularly, the proximal end 20 of the shaft 16 is operably coupled to the internal frame of the housing 4 via a shaft mount 22, see FIG. 4 for example. Shaft mount 22 is operable to rotate with the shaft 12 and is fixed from translating by ribs (not explicitly shown) in the housing 4.

Figure 4:
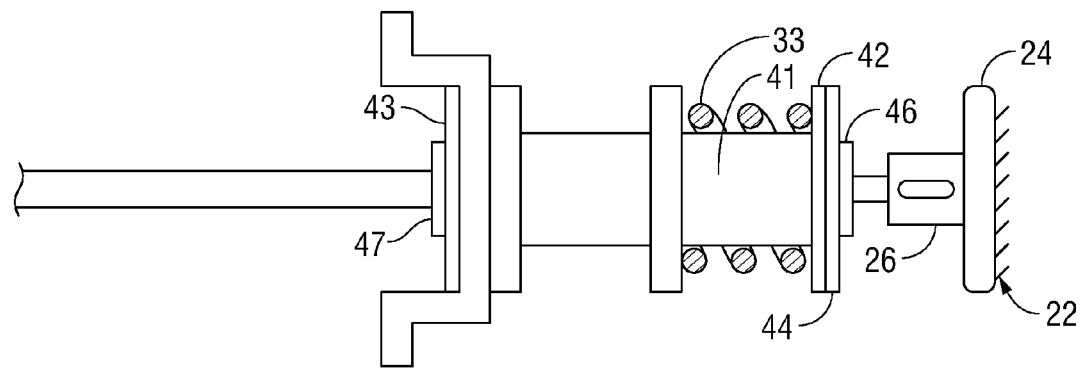
FIG. 4 is schematic view of the rotating assembly in the engaged position.

An outer sleeve or tube 45 (FIGS. 2 and 3) of suitable configuration is coaxially positioned about the shaft 16 and is configured to rotate the shaft 16 when the rotating assembly 6 is rotated. The outer tube 45 is configured to provide a mechanical interface between the shaft 16 and rotating assembly 6 when the rotating assembly 6 is in an engaged or "ready" position such that rotation of the rotating assembly 6 rotates the shaft 16 including the first and second jaw members 39 and 40 (FIG. 1). The outer sleeve 45 includes proximal and distal flanges 46 (FIGS. 2-4) and 47 (FIG. 4), respectively. The proximal flange 46 is configured to contact a proximal clip 44, e.g., an e-clip, that is operably coupled to a mandrel 41 (FIGS. 2-4). Likewise, the distal flange 47 is configured to contact a distal clip 43, e.g., an e-clip, that is operably coupled to mandrel 41 (FIG. 4). Utilizing e-clips for the proximal and distal clips 44 and 43 facilitates positioning a pre-compressed spring 33 therebetween.

Mandrel 41 (FIGS. 2-4) is coaxially positioned about the outer tube 45 of the shaft 16 and supports the rotating assembly 6 and the drive assembly 30 thereon. Mandrel 41 is configured move longitudinally along the outer tube 45 when the movable handle 9 is moved. To this end, mandrel 41 includes a proximal flange 42 (FIGS. 2-4) that is configured to contact a proximal end of spring 33 (FIGS. 2-4) such that the spring 33 compresses thereagainst when the movable handle 9 is moved proximally. A proximal surface of the proximal flange 42 is configured to contact proximal clip 44, FIGS. 2-4. The proximal clip 44 prevents the proximal flange 42 of the mandrel 41 from translating past the proximal flange 46 of the outer tube 45 when the movable handle 9 is moved proximally. That is, the mandrel 41 and/or outer tube 45 are prevented from moving into contact with the shaft mount 22 when the movable handle 9 is moved proximally.

With reference to FIGS. 2-4, shaft mount 22 is illustrated. Shaft mount 22 is fixedly coupled to the internal frame of the housing 4 via one or more suitable coupling methods, e.g., soldering, brazing, ultrasonic welding. In particular, a proximal end 24 (FIGS. 2-4) of the shaft mount 22 includes a generally circumferential configuration and is ultrasonically welded to the internal frame of the housing 4. Shaft mount 22 is configured to allow rotation of the shaft 16 thereabout while maintaining the shaft 16 fixed in orientation about the longitudinal axis "A-A" when the rotating assembly 6 is rotated and/or the movable handle 9 is moved proximally, as described in more detail below. With this purpose, a generally elongated distal end 26 of the shaft mount 22 includes an opening of suitable configuration that is configured to rotatably receive the proximal end 20 of the shaft 16 therein (FIGS. 2-4).

Referring again to FIG. 1, handle assembly 7 includes a fixed handle 28 and movable handle 9. In one particular embodiment, fixed handle 28 is integrally associated with housing 4. Movable handle 9 of handle assembly 7 is ultimately connected to drive assembly 30 (see FIGS. 2-4, for example) to impart movement of the respective first and second jaw members 39 and 40 from the open position (FIG. 1), wherein the first and second jaw members 39 and 40 are disposed in spaced relation relative to one another, to a clamping or closed position (FIG. 3) wherein the first and second jaw members 30 and 40 cooperate to grasp tissue therebetween.

Movable handle 9 is selectively movable about a pivot pin 32 (FIGS. 2 and 3) from a first position relative to fixed handle 28, to a second position in closer proximity to the fixed handle 28 that imparts movement of the first and second jaw members 39 and 40 relative to one another. Proximal movement of the movable handle 9 past a predetermined point places the movable handle 9 in a locked or "latched" position, wherein the first and second jaw members 39 and 40 are maintained in the clamping position. More particularly, when the movable handle 9 is moved proximally a predetermined distance, the locking pins 21a and 21b of a locking feature 21 slidably engage the corresponding ramp portions 17a and 17b, which, in turn, pivots the latch 5 about the pivot pin and the internal frame of the housing 4 against the biasing force of the leaf spring 23. Continued proximal movement of the movable handle 9, causes the locking pins 21a and 21b to engage the cavity 25, which, in turn, maintains the movable handle 9 in a "latched" or locked state (FIG. 3). To release or "unlock" the movable handle 9 from the locked position, the movable handle 9 is moved proximally past the locked position through a release stroke. More particularly, to release the movable handle 9 from the "latched" position, the movable handle 9 is moved proximally through the release stroke to disengage the locking pins 21a and 21b from the cavity 25.

With reference again to FIGS. 2 and 3, the movable handle 9 includes a clevis 34 that forms a pair of flanges, e.g., right upper flange 36a and left upper flange 36b. Unless otherwise stated, it is to be understood that the left upper flange 36b includes the same components and is configured to function similar to that of right upper flange 36a. Right upper flange 36a has an aperture (not explicitly shown) at an upper end thereof for receiving pivot 32 therethrough and mounting the upper end of the movable handle 9 to the housing 4. Upper flange 36a includes a drive flange 37a that is aligned along longitudinal axis "A-A" (see FIGS. 2 and 3) and which abuts the drive assembly 30 such that pivotal movement of the movable handle 9 forces the drive flange 37a proximally against the bias of the spring 33, which, in turn, closes and tensions the first and second jaw members 39 and 40, see FIG. 3.

Continuing with reference to FIGS. 2-4, drive assembly 30 is illustrated. Drive assembly 30 includes proximal and distal collars 48 and 49, respectively. Each of the respective proximal and distal collars 48 and 49 is configured to contact the drive flanges 37a and 37b of the movable handle 9 (FIGS. 2 and 3). Moreover, proximal collar 48 is configured to contact a distal end of the spring 33. The distal end of the spring 33 biases or forces the distal collar 49 against the rotating assembly 6 when the movable handle 9 is in the unlatched position, see FIGS. 2 and 4. In particular, drive assembly 30 is configured to selectively and releasably engage the rotating assembly 6 such that engagement of the rotating assembly 6 with the drive assembly 30 couples the rotating assembly 6 to the shaft 16.

More particularly, when the drive assembly 30 and the rotating assembly 6 are engaged with one another, the rotating assembly 6 and shaft 16 are coupled to one another and the shaft 16 is rotatable about the longitudinal axis "A-A" in a predetermined direction when the rotating assembly 16 is rotated. And, when the rotating assembly 6 and the drive assembly 30 are disengaged from one another, the rotating assembly 6 and shaft 16 are uncoupled from one another and shaft is non-rotatable about the longitudinal axis when the rotating assembly is rotated. To these ends, a frictional interface is present between a proximal surface of the rotating assembly 6 and a distal surface of the distal collar 49 of the drive assembly 30. It is this frictional interface that allows the rotating assembly 6 to rotate the outer tube 45 and, thus, the shaft 16. To avoid "slippage" between the proximal surface of the rotating assembly 6 and the distal surface of the distal collar 49, the coefficient of static friction between these surfaces may range from about 0.2-1.05. As can be appreciated, the compression force provided by the spring 33 may be adjusted to provide any amount of frictional engagement. In accordance with the present disclosure, it has been found that the proximal surface of the rotating assembly 6 and the distal surface of the distal collar 49 may be made from or coated with rubber, steel, copper, brass, cast iron or combination thereof. In the illustrated embodiment, a thin layer of a suitable rubber is operably disposed on the proximal surface of rotating assembly 6 and the distal surface of the distal collar 49. The layers of rubber are in substantial alignment with each other such that in the engaged or "ready" condition the layers of rubber substantially contact one another and remain in contact with one another until the movable handle 9 is moved proximally.

The spring 33 is operably positioned about the mandrel 41 (FIGS. 2-4). More particularly, spring 33 is positioned between proximal collar 48 of the drive assembly 30 and proximal flange 42 of the mandrel 41. As noted above, the spring 33 is configured to bias the distal collar 49 of the drive assembly 30 into engagement with the rotating assembly 6. In the embodiment illustrated in FIGS. 1-4, the spring 33 is a compression spring. In certain embodiments, drive assembly 30 including the spring 33 is configured to provide a consisitent closure force on the first and second jaw members 39 and 40, respectively, in a range from about 3 kg/cm$^2$ to about 16 kg/cm$^2$ when the movable handle 9 is in the latched position.

Referring again to FIG. 1-4, rotating assembly 6 is illustrated including two halves 6a and 6b which, when assembled, form the rotating assembly 6. Rotating assembly 6 is integrally associated with the housing 4 and is rotatable in either a clockwise or counter clockwise direction about the longitudinal axis "A-A" (FIG. 1) to impart movement of the shaft 16 including the first and second jaw members 39 and 40. The rotating assembly 6 may be formed from any suitable material including but not limited to plastic, metal, etc. In the illustrated embodiment, the rotating assembly 6 is made from a relatively rigid plastic and, as noted above, includes a layer of suitable rubber on the proximal surface thereof. To facilitate rotation, a plurality of raised protrusions or detents is disposed along an outer peripheral edge of the rotating assembly 6.

Rotating assembly 6 is rotatably supported on the mandrel 41. Rotating assembly 6 is operably coupled to the shaft 16 via the outer tube 45. More particularly, when the distal collar 49 is forced or "pressed" against the rotating assembly 6, the rotating assembly 6 presses against the distal clip 43, which, in turn, presses against the distal flange 47 of the outer tube 45. This pressing of the distal flange 47 engages the outer tube 45 with the shaft 16 such that the shaft 16 is rotatable about the longitudinal axis "A-A" when the rotating assembly 6 is rotated. As can be appreciated, the combination of the rotating assembly 6 and distal collar 49 configured to press thereagainst is configured to function similar to that of a "clutch mechanism" typically utilized in an automobile Referring again to FIGS. 1 and 3, first and second jaw members 39 and 40 are operatively and pivotably coupled to each other and located adjacent the distal end 18 of shaft 16. For illustrative purposes, the end effector 14 is shown including a unilateral jaw configuration, i.e., first jaw member 39 is movable with respect to second jaw member 40 that is non-movable or stationary with respect to first jaw member 39. In the illustrated embodiment, the first jaw member 39 is movable from a normally open configuration to the clamping configuration when the movable handle 9 is moved proximally, see FIGS. 1 and 3, respectively. Respective electrically conductive seal plates 50 and 52 are operably supported on and secured to jaw housings 54 and 56 of respective first and second jaw members 39 and 40, see FIG. 1.

In use, movable handle 9, initially, is in an unlocked or unlatched position. In the unlocked or unlatched position, the distal collar 49 of the drive assembly 30 is engaged with the rotating assembly 6 via the biasing force provided by the spring 33. As noted above, this engages the outer tube 45 with the shaft 16. To facilitate positioning tissue between the first and second jaw members 39 and 40, respectively, rotating assembly 6 may be rotated about the longitudinal axis "A-A." With tissue is positioned between the first and second jaw members 39 and 40, movable handle 9 is moved proximally a predetermined distance to engage the locking member 21 with the latch 5. With the locking member 21 and latch 5 in the engaged condition, the first and second jaw members 39 and 40 remain in the clamping configuration.

In the engaged position, the drive assembly 30 is out of engagement with the rotating assembly 6, which, in turn, causes the rotating assembly 6 to move out of engagement with the distal flange 47 of the outer tube 45; this, in turn, uncouples the rotating assembly 6 from the shaft 16. With the rotating assembly 6 uncoupled from the shaft 16, rotation of the rotating assembly 6 results in the rotating assembly 6 spinning freely about the mandrel 41 (i.e., rotating assembly 6 is temporarily disabled) and the shaft 19 not rotating about the longitudinal axis "A-A." As can be appreciated, with the rotating assembly 6 temporarily disabled during an electrosurgical procedure, the likelihood of inadvertent movement or rotation of the shaft 19 and/or first and second jaw members 39 and 40 is greatly diminished and/or eliminated.

From the foregoing, and with reference to the various figure drawings, those skilled in the art will appreciate that certain modifications can also be made to the present disclosure without departing from the scope of the same. For example, and with reference to FIG. 5, an endoscopic forceps 102 may include a rotating assembly 106 in operable communication with proximal external wheel 101a (gear wheel 101a) and distal external gear wheel 101b (gear wheel 101b). The endoscopic forceps 102 with the rotating assembly 106 is substantially similar to the endoscopic forceps 2 with the rotating assembly 6. As a result thereof, only those features unique to endoscopic forceps 102 with the rotating assembly 6 are described in detail.

Figure 5:
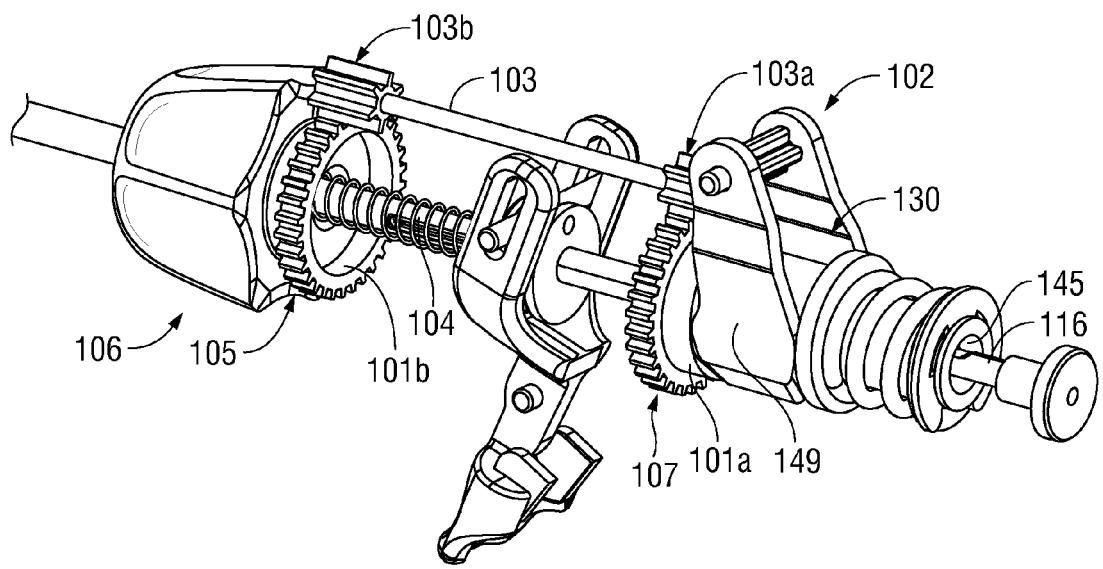
FIG. 5 is partial, left perspective view of an endoscopic forceps including a rotating assembly according to another embodiment of the present disclosure.

Continuing with reference with FIG. 5, unlike rotating assembly 6, rotating assembly 106 is disposed at a distal end of the housing of the endoscopic forceps 102 and includes a generally conical configuration. Rotating assembly 106 is operably coupled to or includes gear wheel 101b and is configured such that rotation of the rotating assembly 106 in a predetermined direction rotates the gear wheel 101b while simultaneously rotating gear wheel 101a, as described in more detail below.

Gear wheel 101b is rotatably supported on an outer drive sleeve or tube 104 of the drive assembly 130. A plurality of teeth 105 is disposed on an outer peripheral edge of the gear wheel 101b. Gear wheel 101b is in operable communication with the gear wheel 101a via a coupling rod 103.

Coupling rod 103 operably couples to the rotating assembly 106 via a bushing and pin configuration (not shown) that is configured to allow coupling rod 103 to rotate with respect to the rotating assembly 106. That is, the bushing and pin configuration allows the coupling rod 103 to rotate with respect to the gear wheel 101b and the rotating assembly 6 as the rotating assembly 6 is rotated. Coupling rod 103 includes proximal and distal pluralities of teeth 103a and 103b. The plurality of teeth 103b is configured to mesh with the plurality of teeth 105 on the gear wheel 101b. Similarly, the plurality of teeth 103a is configured to mesh with a plurality of teeth 107 on the gear wheel 101a.

Gear wheel 101a functions similar to rotating assembly 6 in that gear wheel 101a is positioned between the distal collar 149 of the drive assembly 130 and a distal flange 142 of the outer tube 145. Gear wheel is disposed within the confines of the housing of the endoscopic forceps 102.

In use, the movable handle (not explicitly shown), initially, is in an unlocked or unlatched position. In the unlocked or unlatched position, the distal collar 149 of the drive assembly 130 is engaged with the gear wheel 101a via the biasing force provided by the spring 133. As noted above, this engages the outer tube 145 with the shaft 116. To facilitate positioning tissue between the first and second jaw members 39 and 40, respectively, rotating assembly 106 may be rotated about the longitudinal axis "A-A." Rotating the rotating assembly 106 rotates the gear wheel 101b, which, in turn, rotates the coupling rod 103 and the gear wheel 101a. With tissue positioned between the first and second jaw members 39 and 40, the movable handle is moved proximally a predetermined distance to the locked position. As can be appreciated, with the movable handle in the locked position, the drive assembly 130 is out of engagement with the gear wheel 101a, which, in turn, causes the gear wheel 101a to move out of engagement with the distal flange 147 of the outer tube 145; this, in turn, uncouples the rotating assembly 106 from the shaft 116. With the rotating assembly 106 uncoupled from the shaft 116, rotation of the rotating assembly 106 results in the rotating assembly 106 including coupling rod 103 and the gear wheels 101a and 101b spinning "freely" about the outer drive tube 104 and/or the mandrel 141 (i.e., rotating assembly 106 is temporarily disabled) and the shaft 19 not rotating about the longitudinal axis "A-A."

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
   a housing having a shaft extending therefrom, the shaft defining a longitudinal axis therethrough;
   an end effector assembly operably coupled to a distal end of the shaft;
   a rotating assembly operably coupled to the shaft and configured to rotate the shaft; and
   a drive assembly configured to selectively engage the rotating assembly, wherein engagement of the rotating assembly with the drive assembly couples the rotating assembly to the shaft such that the shaft is rotatable about the longitudinal axis when the rotating assembly is rotated, and wherein the drive assembly is configured to selectively disengage from the rotating assembly by uncoupling the rotating assembly from the shaft rendering the shaft unrotatable relative to the housing.

2. A surgical instrument according to claim 1, wherein the shaft includes an outer tube and the rotating assembly includes a mandrel coaxially positioned around the outer tube that is configured to support the rotatable assembly and the drive assembly thereon.

3. A surgical instrument according to claim 2, wherein the drive assembly includes a proximal collar and a distal collar and the rotating assembly is positioned between the distal collar of the drive assembly and a distal clip operably disposed on the mandrel.

4. A surgical instrument according to claim 3, wherein a spring is positioned between the proximal collar of the drive assembly and a proximal flange of the mandrel, the spring configured to at least bias the distal collar of the drive assembly into engagement with the rotating assembly.

5. A surgical instrument according to claim 4, wherein the end effector assembly includes first and second jaw members, at least one of the first and second jaw members movable relative to the other from an open position, wherein the first and second jaw members are disposed in spaced relation relative to one another, to a clamping position, wherein the first and second jaw members cooperate to grasp tissue therebetween.

6. A surgical instrument according to claim 5, wherein the spring is a compression spring that cooperates with the drive assembly to provide a closure force on the first and second jaw members in the range from about 3 kg/cm$^2$ to about 16 kg/cm$^2$ when the movable handle is in the latched position.

7. A surgical instrument according to claim 3, wherein the drive assembly is operably coupled to a movable handle associated with the housing, the drive assembly configured such that a predetermined amount of proximal movement of the movable handle moves the distal collar of the drive assembly out of engagement with the rotating assembly such that the rotating assembly spins freely about the mandrel when rotated.

8. A surgical instrument according to claim 7, wherein a shaft mount operably couples to the housing and the shaft, the shaft mount configured to allow rotation of the shaft thereabout when the rotating assembly is rotated and configured to prevent translation of the shaft along the longitudinal axis when the movable handle is moved proximally.

9. A surgical instrument according to claim 7, further comprising a latch configured to releasably engage the movable handle, the latch operably coupled to an internal frame of the housing.

10. A surgical instrument according to claim 9, wherein the latch is pivotably coupled to the internal frame of the housing and includes a resilient member configured to bias the latch in a direction towards the shaft.

11. A surgical instrument according to claim 10, wherein the resilient member is a leaf spring.

12. A surgical instrument according to claim 9, wherein a locking feature is operably coupled to a proximal end of the movable handle and is configured to selectively and releasably engage the latch.

13. A surgical instrument, comprising:
an end effector assembly;
a rotating assembly operably coupled to the end effector assembly and configured to rotate the end effector assembly; and
a drive assembly operably coupled to the end effector assembly and configured to selectively engage the rotating assembly, wherein engagement of the rotating assembly with the drive assembly couples the rotating assembly to the end effector assembly such that the end effector assembly is rotated when the rotating assembly is rotated, wherein the drive assembly is configured to selectively disengage the rotating assembly rendering the end effector assembly unrotatable relative to the housing.

14. A surgical instrument according to claim 13, further including an outer tube, wherein the rotating assembly includes a mandrel coaxially positioned around the outer tube that is configured to support the rotatable assembly and the drive assembly thereon.

15. A surgical instrument according to claim 14, further comprising a coupling rod including proximal and distal external gear wheels disposed thereon, the proximal external gear wheel of the coupling rod configured to mesh with a proximal external gear wheel of the rotating assembly, and the distal external gear wheel of the coupling rod configured to mesh with a distal external gear wheel of the rotating assembly such that rotation of the rotating assembly rotates the end effector assembly.

16. A surgical instrument according to claim 15, wherein the drive assembly includes a proximal collar and a distal collar and the mandrel includes a distal clip and wherein the proximal external gear wheel of the rotating assembly is positioned between the distal collar of the drive assembly and the distal clip.

17. A surgical instrument according to claim 16, wherein a spring is positioned between the proximal collar of the drive assembly and a proximal flange of the mandrel, the spring configured to at least bias the distal collar of the drive assembly into engagement with the proximal external gear wheel of the rotating assembly.

18. A surgical instrument according to claim 13, wherein the end effector assembly includes first and second jaw members, at least one of the first and second jaw members movable relative to the other jaw member from an open position, wherein the first and second jaw members are disposed in spaced relation relative to one another, to a clamping position, wherein the first and second jaw members cooperate to grasp tissue therebetween.

19. A surgical instrument, comprising:
an end effector assembly;
a rotating assembly operably coupled to the end effector assembly and configured to rotate the end effector assembly;
a drive assembly operably coupled to the end effector assembly and configured to selectively engage the rotating assembly, wherein engagement of the rotating assembly with the drive assembly couples the rotating assembly to the end effector assembly such that the end effector assembly is rotated when the rotating assembly is rotated, the rotating assembly including a mandrel coaxially positioned around an outer tube configured to support the rotatable assembly and the drive assembly thereon; and
a coupling rod including proximal and distal external gear wheels disposed thereon, the proximal external gear wheel of the coupling rod configured to mesh with a proximal external gear wheel of the rotating assembly, and the distal external gear wheel of the coupling rod configured to mesh with a distal external gear wheel of the rotating assembly such that rotation of the rotating assembly rotates the end effector assembly.

20. A surgical instrument, comprising:
a housing having a shaft extending therefrom, the shaft defining a longitudinal axis therethrough;
an end effector assembly operably coupled to a distal end of the shaft;
a rotating assembly operably coupled to the shaft and configured to rotate the shaft; and
a drive assembly configured to selectively engage the rotating assembly, wherein engagement of the rotating assembly with the drive assembly couples the rotating assembly to the shaft such that the shaft is rotatable about the longitudinal axis when the rotating assembly is rotated, and wherein the drive assembly includes a proximal collar and a distal collar and the rotating assembly is positioned between the distal collar of the drive assembly and a distal clip operably disposed on the mandrel and wherein the shaft includes an outer tube and the rotating assembly includes a mandrel coaxially positioned around the outer tube that is configured to support the rotatable assembly and the drive assembly thereon.

21. A surgical instrument according to claim 20, wherein a spring is positioned between the proximal collar of the drive assembly and a proximal flange of the mandrel, the spring configured to at least bias the distal collar of the drive assembly into engagement with the rotating assembly.

22. A surgical instrument according to claim 21, wherein the end effector assembly includes first and second jaw members, at least one of the first and second jaw members movable relative to the other from an open position, wherein the first and second jaw members are disposed in spaced relation relative to one another, to a clamping position, wherein the first and second jaw members cooperate to grasp tissue therebetween.

23. A surgical instrument according to claim 22, wherein the spring is a compression spring that cooperates with the drive assembly to provide a closure force on the first and second jaw members in the range from about 3 kg/cm$^2$ to about 16 kg/cm$^2$ when the movable handle is in the latched position.

24. A surgical instrument according to claim 20, wherein the drive assembly is operably coupled to a movable handle associated with the housing, the drive assembly configured such that a predetermined amount of proximal movement of the movable handle moves the distal collar of the drive assembly out of engagement with the rotating assembly such that the rotating assembly spins freely about the mandrel when rotated.

25. A surgical instrument according to claim 24, wherein a shaft mount operably couples to the housing and the shaft, the shaft mount configured to allow rotation of the shaft thereabout when the rotating assembly is rotated and configured to prevent translation of the shaft along the longitudinal axis when the movable handle is moved proximally.

26. A surgical instrument according to claim 24, further comprising a latch configured to releasably engage the movable handle, the latch operably coupled to an internal frame of the housing.

27. A surgical instrument according to claim 26, wherein the latch is pivotably coupled to the internal frame of the housing and includes a resilient member configured to bias the latch in a direction towards the shaft.

28. A surgical instrument according to claim 27, wherein the resilient member is a leaf spring.

29. A surgical instrument according to claim 26, wherein a locking feature is operably coupled to a proximal end of the movable handle and is configured to selectively and releasably engage the latch.

* * * * *